United States Patent
Gårdhagen et al.

(10) Patent No.: US 6,192,766 B1
(45) Date of Patent: Feb. 27, 2001

(54) APPARATUS, SYSTEM AND METHOD FOR THE DETECTION OF AN ANALYTE IN AIR

(75) Inventors: Peter Gårdhagen, Nora; Magnus Samuelsson, Eskilstuna; Arne Alm, Eskiltuna; Åke Jansson, Eskilstuna; Johan Arnell, Eskilstuna; Claes Andersson; Erik Johansson, both of Karlskoga, all of (SE)

(73) Assignee: Biosensor Applications Sweden AB (publ), Oregbro (SE)

( * ) Notice: Subject to any disclaimer, the term of this patent is extended or adjusted under 35 U.S.C. 154(b) by 0 days.

(21) Appl. No.: 09/096,531

(22) Filed: Jun. 12, 1998

Related U.S. Application Data
(60) Provisional application No. 60/049,449, filed on Jun. 12, 1997.

Foreign Application Priority Data
Jun. 24, 1997 (SE) .................................................. 9702407

(51) Int. Cl.[7] ..................................................... G01N 1/00
(52) U.S. Cl. ......................................................... 73/863.12
(58) Field of Search ........................... 73/864.34, 863.12, 73/863.21, 863.23, 864.81, 31.01, 31.07, 23.41, 23.42; 422/83, 88

(56) References Cited

U.S. PATENT DOCUMENTS

| | | | |
|---|---|---|---|
| 3,996,008 | * 12/1976 | Fine et al. | 73/23.35 |
| 4,128,008 | * 12/1978 | Linenberg | 73/863.12 |
| 5,092,156 | 3/1992 | Miskolczy . | |
| 5,138,889 | 8/1992 | Conrad . | |
| 5,390,529 | * 2/1995 | Ghiselli | 73/23.41 |

FOREIGN PATENT DOCUMENTS

| | | |
|---|---|---|
| 0 401 861 A2 | 12/1990 | (EP) . |
| 04227014 | 8/1992 | (EP) . |
| 2 660 873 A1 | 10/1991 | (FR) . |

OTHER PUBLICATIONS
Josefson et al., Anal. Chem. 56:764–768 (1984).

* cited by examiner

*Primary Examiner*—Robert Raevis
(74) *Attorney, Agent, or Firm*—Bacon & Thomas (57) ABSTRACT

An apparatus, a system and a method for the detection of an analyte in air comprising an air sampling system (1) comprising a mouthpiece (10) and a fan, a first enrichment stage (11) for enrichment of the analyte comprising a thermally regulated adsorption/desorption filter (20) creating a non-laminar gas flow for adsorption of the analyte, a heat source for heating the filter to evaporate the analyte, a second enrichment stage (30) for the further enrichment of the gaseous analyte comprising a cold trap (32) for condensing the analyte, extraction of the condensed material with a solvent, and collecting the solution, and analyzing the collected liquid sample with an analytical detection system, are disclosed. Further, an adsoption/desorption filter creating a non-laminar gas flow comprising a winding (21) of a resistance wire coated with an active material electric heating of the wire, is described. A specific application is detection of a gaseous component of explosives or mines, e.g. TNT, in air.

6 Claims, 7 Drawing Sheets

Fig. 1

SCALE=1.000

APPARATUS, SYSTEM AND METHOD FOR THE DETECTION OF AN ANALYTE IN AIR

CROSS REFERENCE TO RELATED APPLICATION

This application claims benefit of the filing data of provisional application number 60/049,449 filed Jun. 12, 1997.

The present invention relates to an apparatus, a system and a method for the detection of an analyte in air. The invention is particularly concerned with the detection of dangerous chemicals such as explosives, mines, bombs, war gases and narcotics.

BACKGROUND

It is difficult to selectively detect small amounts of a gaseous analyte in air, and it is particularly important to do so when the location of dangerous chemicals is to be determined.

For example, since World War II, mine detection has been mostly carried out with the help of metal seekers that detect small amounts of metal contained in most mines. As a result of the development of anti-personal mines with less and less metal, the sensitivity of a metal seeker has been enhanced to give alarm for less than one gram of metal. However, at this sensitivity level metal fragments in the ground will block its use in most mined terrain by giving a false alarm.

Another method for mine detection, and narcotics detection, which has been successfully applied, has been the use of trained dogs. But even the best dog can only work for short periods with full attention and with long rest periods in between. Well trained dogs are also very expensive.

It would be desirable to have an apparatus, a system and a method for the selective detection of small amounts of an analyte in air for many applications, e.g. in the process industry for the detection of specific contamination or leakage, in the airport safety control, customs and police work for the detection of narcotics and bombs, and in clearing the terrain of mines and bombs after a war situation.

DESCRIPTION OF THE INVENTION

The present invention provides an apparatus, a system and a method for the selective detection of an analyte in a sample of air. The sample of air is collected at a suspected location. The possible specific analyte is enriched from the air sample in accordance with the present invention, and finally the specific analyte of interest is analyzed from a small amount of liquid.

Figure 1:
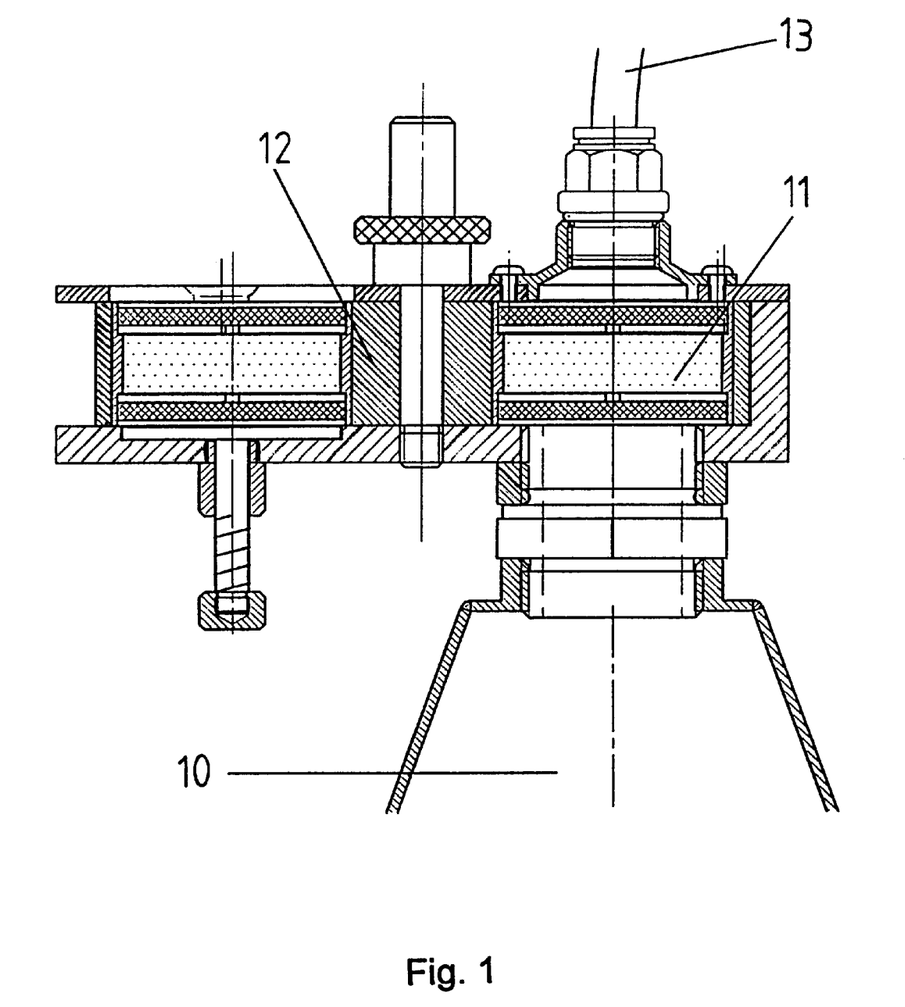
Figure 2A:
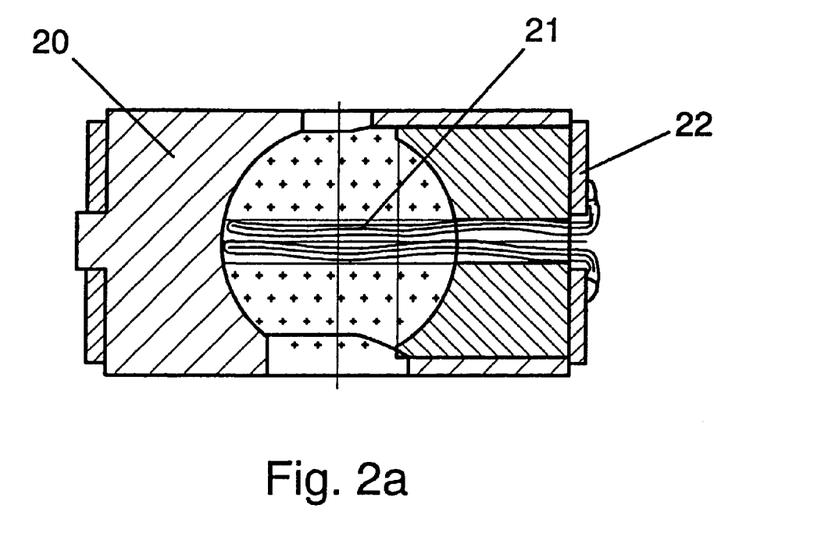
Figure 2B:
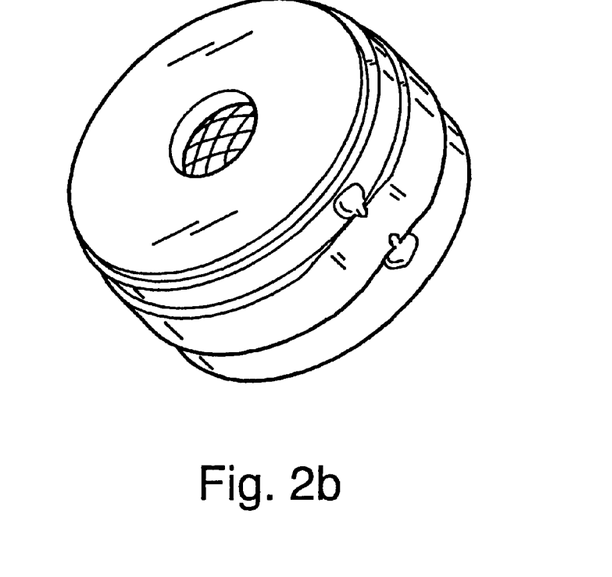
Figure 3A:
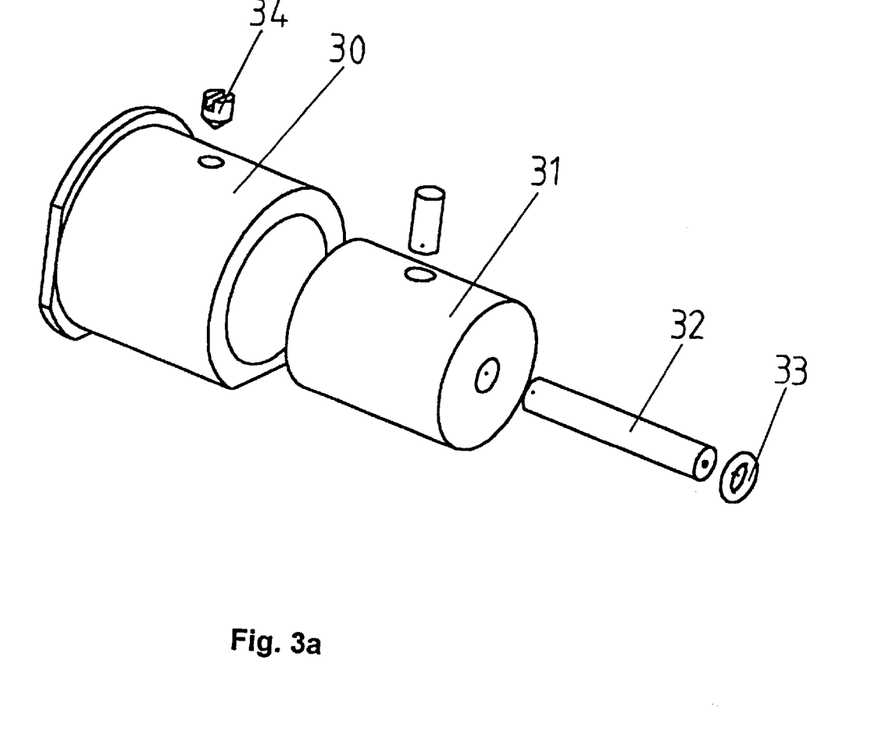
FIG. 3a. shows a side view of the parts of a second enrichment stage comprising a cold trap (e.g. of a hydrophilic material). The cold trap is composed of a quartz capillary (32) in a heat sink of stone (31) mounted in a plastic housing (30). The whole unit is held together by a single screw (34) cooperating with an elastic (rubber) distance pin. An O-ring (33) is also mounted at the tip of the capillary (32) as a seat to the adsorption filter from the first enrichment stage, FIG. 3b. shows a cross-section of the second enrichment stage.
Figure 3B:
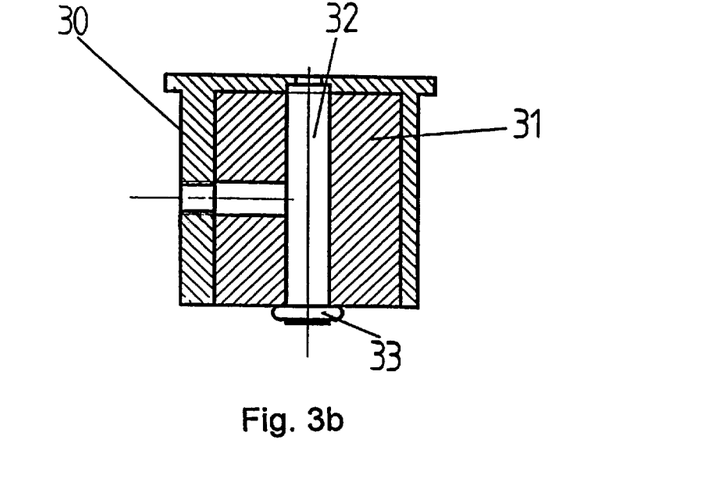
Figure 4A:
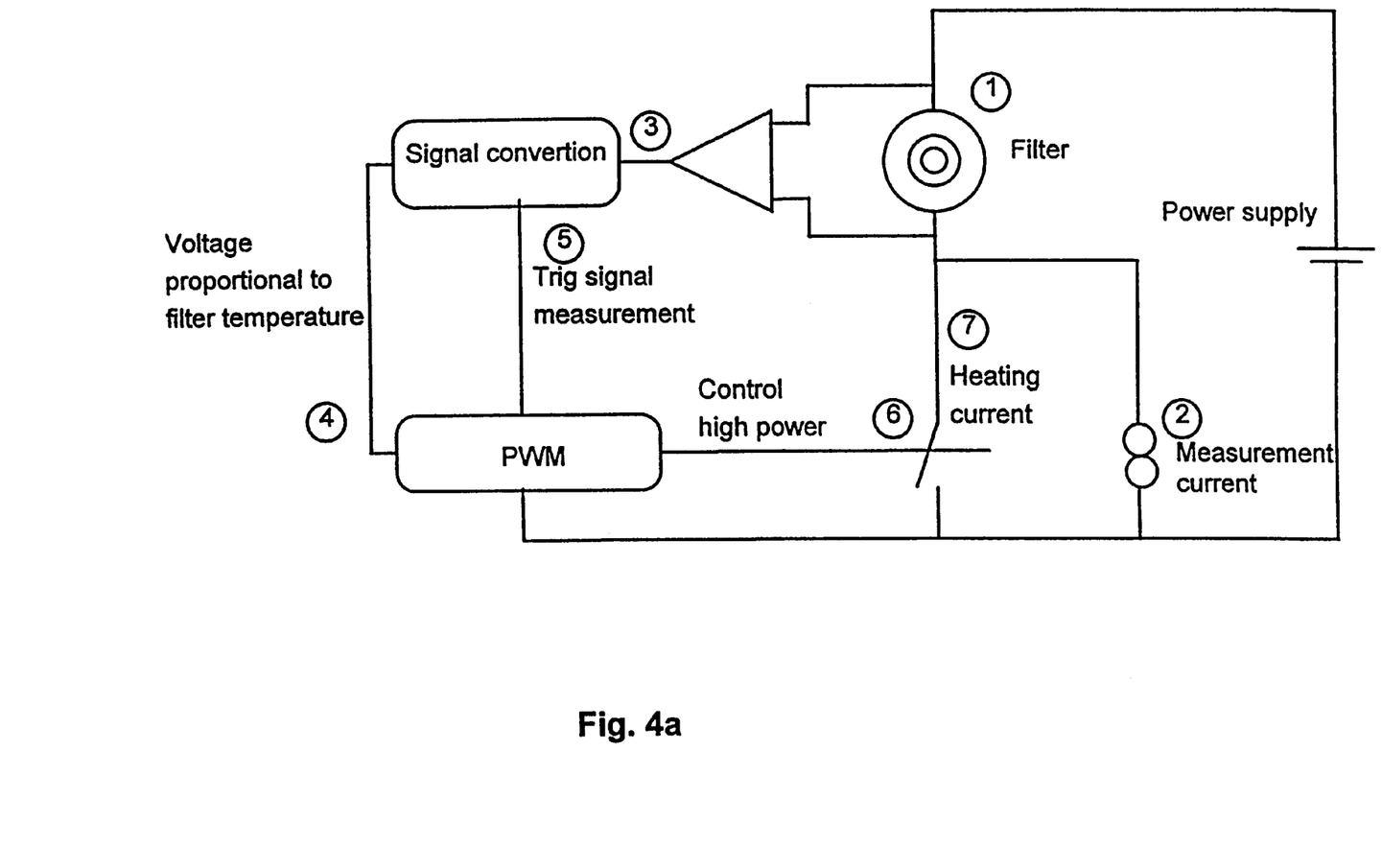
Figure 4B:
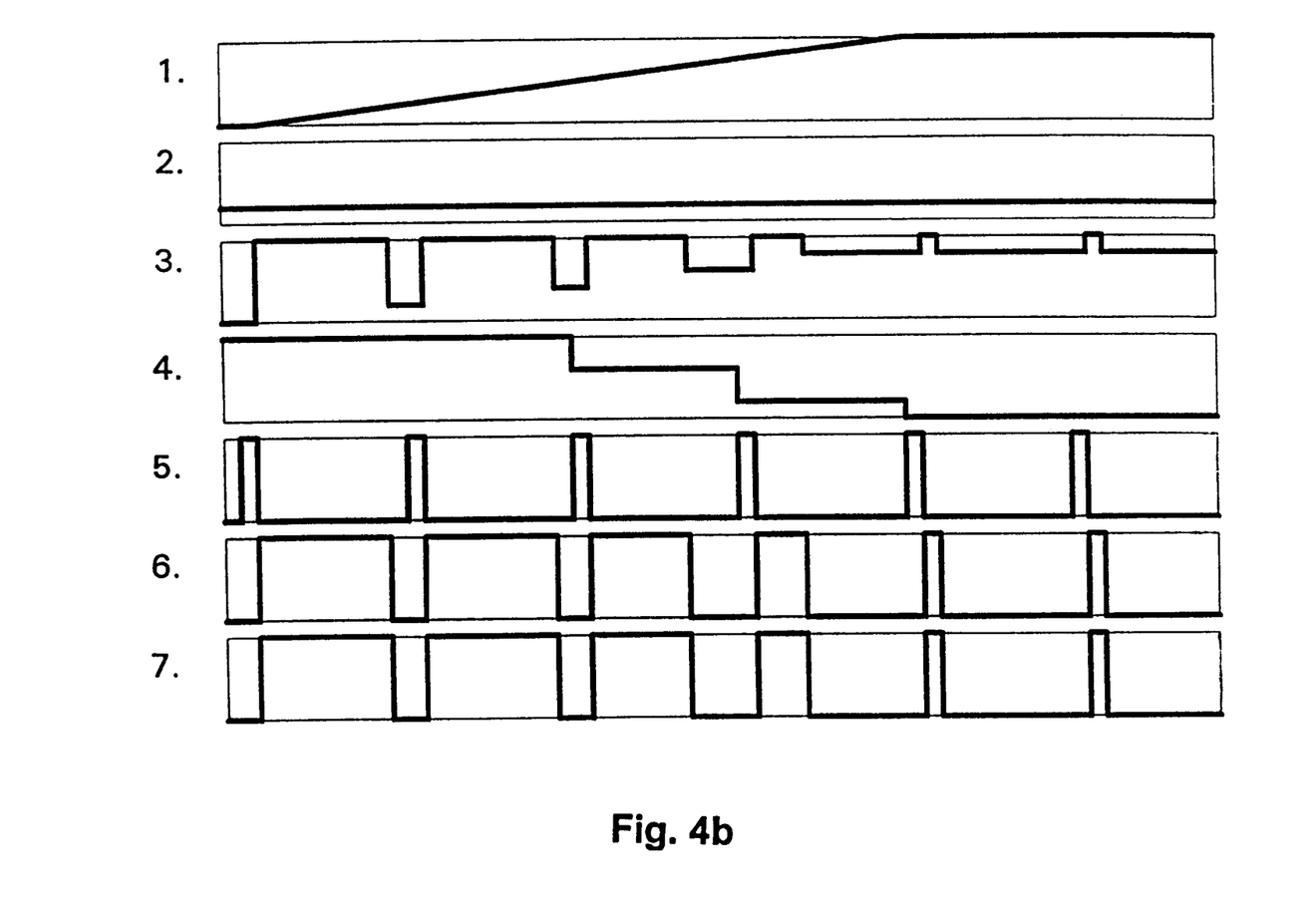
Figure 5A:
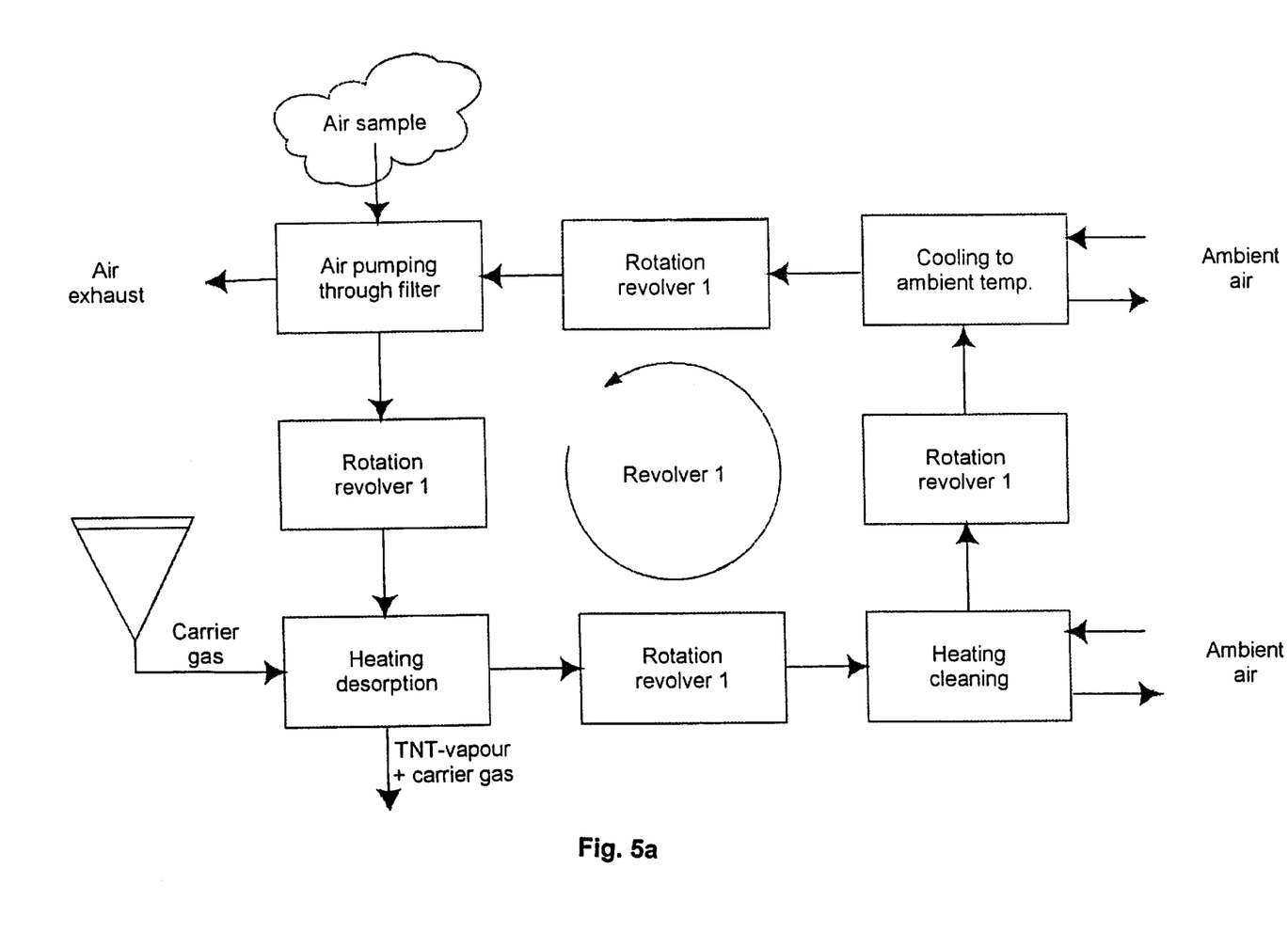
FIGS. 5a+5b., shows a schematic presentation of an automated system for air sampling and enrichment of analyte according to the invention.
Figure 5B:
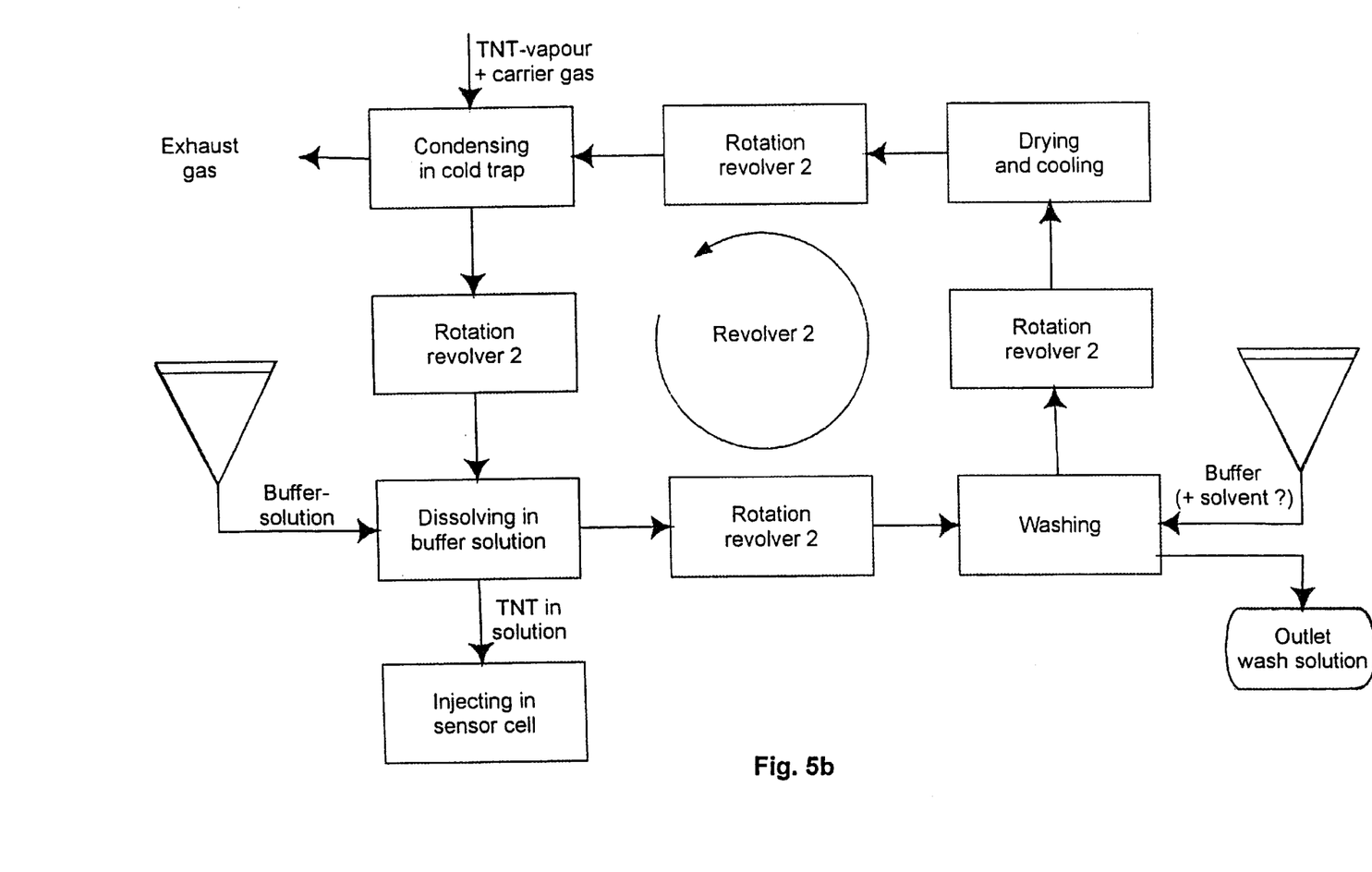

One aspect of the invention is concerned with an apparatus for the detection of an analyte in air comprising
an air sampling system (1) for collecting an air sample comprising a mouthpiece (10) and a fan,
means for transport of the air through a first enrichment state (11) for enrichment of the analyte comprising a thermally regulated adsorption/desorption filter creating a non-laminar gas flow for adsorption of the analyte on the filter surfaces, encased in a housing having a gas inlet and a gas outlet connected to valves, and a heat source for heating the filter to a temperature high enough to evaporate the analyte but low enough to avoid decomposition of the analyte,
means for transport of the desorbed analyte from the filter to a second enrichment stage for the further enrichment of the gaseous analyte comprising a cold trap (32) for condensing the analyte, means for extraction of the condensed material with a solvent, and means for collecting the solution enriched in analyte from the cold trap, and means for transport of the collected liquid sample to an analytical detection system for the detection of the analyte.

In a preferred embodiment of this aspect of the invention, the valves are substituted for a revolver, the first enrichment stage is reconditioned by cooling gas, and the second enrichment stage is connected to a revolver and reconditioned by washing the cold trap with a solvent.

Another aspect of the invention is concerned with an adsorption/desorption filter creating a non-laminar gas flow, which comprises a gas inlet and a gas outlet connected to a housing (20) in which a winding (21) of a resistance wire, such as a copper wire, coated with an active (insulating) material having affinity for an analyte to be tested, such as Teflon®, is encased, and two connector bands (22) attached to the ends of the wire for electric heating of the wire to a temperature that provides a temperature on the surface of the active material at which the analyte is desorbed without decomposition.

A further aspect of the invention is concerned with a system for the detection of an analyte in air comprising
an air sampling system comprising a mouthpiece and a fan,
a first enrichment stage for enrichment of the analyte comprising a thermally regulated adsorption/desorption filter creating a non-laminar gas flow comprising a housing having a gas inlet and a gas outlet connected to valves, and
a heat source for heating the filter to a temperature high enough to evaporate the analyte but low enough to avoid decomposition of the analyte,
a second enrichment stage for the further enrichment of the analyte comprising a cold trap for condensing the analyte, extraction of the condensed material with a solvent, and collecting the solution enriched in analyte from the cold trap, and
an analytical detection system for the detection of the analyte from a liquid sample.

In a preferred embodiment of this aspect of the invention, the valves are substituted for a revolver, the first enrichment stage is reconditioned by cooling gas, and the second enrichment stage is connected to a revolver and reconditioned by washing the cold trap with a solvent.

Yet another aspect of the invention is concerned with a method of detecting an analyte in air comprising
sampling of air with an air sampling system comprising a mouthpiece and a fan,
passing the air to a first enrichment stage where the analyte is adsorbed on the surfaces of a thermally regulated adsorption/desorption filter creating a non-laminar gas flow,
heating the filter surfaces to a temperature high enough to evaporate the analyte but low enough to avoid decomposition of the analyte,
flushing the filter with a small amount of an inert gas, such as nitrogen or air,
passing the vapor from the first enrichment stage to a second enrichment stage for the further enrichment of the analyte by condensation in a cold trap,
flushing the cold trap with a small amount of solvent to dissolve the condensed material,
collecting the small amount of solution containing the analyte in an container, and
analyzing the presence of analyte in the container with the aid of an analytical detection system for the detection of the analyte in liquid sample.

In a preferred embodiment the analyte is a gaseous component of explosives or mines, such as TNT (2,4,6-trinitrotoluene), RDX (1,3,5-trinitro-1,3,5-triazacyclohexane) or PETN (pentaerythritoltetranitrate).

The invention is also concerned with the use of the apparatus and system, respectively, each according to the invention, for the detection of a gaseous component of explosives or mines, e.g. TNT (2,4,6-trinitrotoluene), RDX (1,3,5-trinitro-1,3,5-triazacyclohexane) or PETN (pentaerythritoltetranitrate), and use of the adsorption/desorption filter according to the invention in an apparatus, system and method for the detection of an analyte in air.

The invention will now be illustrated with the air of the following description of specific embodiments, related drawings and examples. However, the invention should not be considered to be limited to such exemplification.

An apparatus, a system and a method of the invention preferably comprises the following elements 1) An Air Sampling System Comprising
   mouth piece
   dust filter (optional)
   hygrometer (optional)
   fan (or external pump)
   injection valve (preferred embodiment)
2) A First Enrichment Stage Comprising
   adsorption/desorption filter of active (insulating) (e.g. hydrophobic) material
   valves (revolver)
   heater
   filter reconditioning
3) A Second Enrichment Stage Comprising
   cold trap
   solution
   pump (optionally manual injection)
   washing (reconditioning of cold trap)
4) One or more analytical detection system(s), such as a) gas chromatograph or b) biosensor(s) (each) comprising
   flow cell
   quartz crystal
   surface antibody coating, the antibody being specific for an binding to
   the specific analyte of interest
5) Optional Signal Processing Comprising, in the Case of 4) b),
   reference oscillator
   CPU
   serial communication link
6) Optional Man Machine Interface Comprising
   acoustic alarm
   presentation LEDs
   control switch
7) Optional Support Systems for Each of the Elements 1 to 6, comprising
   structure
   power supply The method of the invention starts with the sampling of air, which possibly contains or is suspected to contain a specific analyte of interest, with air sampling.

Air Sampling System

Air is collected with the help of a fan (or ejector pump), through a mouthpiece held at a suspected location, such as just over the ground of a suspected mine, and the air is transported, if necessary, through a filter for dust separation, to the first enrichment stage and through its adsorption/desorption filter to an exhaust facing away from the ground. The air sampling system may also include a calibration and test system, optionally controlled from the signal processing, for automated injection of a small, calibrated amount of analyte, e.g. TNT (2,4,6-trinitrotoluene) vapor or TNT solution, into the airflow ahead of the first enrichment stage. The air sampling system should have a neutral surface, or surface coating, with regard to the analyte content of the air stream, at least for the duration of one sample in the sampling system (gilding has been used in prototype).

Preferably, the moisture content of the air inflow has to be known, and sometimes adjusted, to facilitate the subsequent process control. A hygrometer may be placed within the air inlet or in connection with the air sampling system, for instance on the outside of the mouthpiece.

The First Enrichment Stage operates with an (e.g. hydrophobic) adsorption/desorption filter which should be of a material (etched polytetrafluoroethylene, Teflon®, used in prototype) that, with high efficiency, adsorbs the analyte, such as TNT, from air at the normal sampling temperature, and desorbs it again when it is heated to a higher temperature, which however should be lower than the decomposition temperature of the analyte (e.g. TNT).

In an embodiment, the construction of the filter, in the first enrichment stage, is made from an etched hydrophobic and electrically insulating material deposited on metal wire. This has many advantages: The etched material gives a very high effective area for adsorption and the metal wire core allows very fast electrical heating for desorption. In addition, the use of a hydrophobic material will allow most unwanted chemicals and water-vapor to pass through the first stage, and only hydrophobic vapors are trapped by the filter.

During the adsorption stage the air flow through the filter is driven by the fan (pump) in the air sampling system. During the desorption stage the transport and vaporization of the analyte, such as TNT, in the filter is driven by a small amount of an inert gas together with the heat expansion of the trapped air, thus giving an enrichment of analyte (e.g. TNT) vapor in the process gas (dry nitrogen was used in prototype).

The adsorption-desorption filter in the first enrichment stage will function for a limited number of temperature cycles and must therefore be replaced at regular service intervals.

The Second Enrichment Stage contains a (e.g. hydrophilic) cold trap (quartz at ambient temperature) for condensation of the analyte (e.g. TNT) vapor from the first enrichment stage, and a pump system for the transport of a drop of a solvent, such as water, through the cold trap into a container for analysis. The type of the container depends on the type of method and equipment selected for the analysis. In case piezoelectric determination is selected, the container may be one or several biosensor cell(s).

In case the analyte is TNT, the water solution will normally not accept such a hydrophobic chemical, but TNT is polar enough to have an acceptable solubility at the actual low concentrations. The use of a hydrophilic second enrichment stage thus eliminates most of the disturbing hydrophobic chemicals that passed the first enrichment stage.

Analytical Detection System

The condensed material in the cold trap is flushed with a small amount of solvent to dissolve the material, and the solution containing the analyte is collected in a container, e.g. an air sampling tube of a gas chromatograph or a flow cell of a biosensor system, depending on which type of analytical detection system is to be used.

In the prototype, the cold trap is manually washed with buffer solution, which is then injected into the container for analysis on a gas chromatograph or a biosensor system.

Gas chromatographs are standard laboratory equipment, and a biosensor system which has been used in Example 2 in the Experimental part of this description is described below.

Biosensor System

The Biosensor system used in the piezoelectric determination of the analyte, comprises a flow cell, in which the solvent/water solution, from the second enrichment stage, passes over the surface of an oscillating quartz crystal, coated with a layered structure exposing an antibody complex active against the analyte, e.g. TNT, to the solution. The antibodies bind to the analyte, e.g. TNT, in the solution, and the weight difference, at the surface of the crystal, gives a slight change in the resonance frequency in the electronic circuit incorporating the crystal. When the number of antibodies available for binding to the analyte is reduced due to the complex formation with the analyte in the test solution, the cell ceases to function. Then, the quartz crystal is replaced with another one which has a fresh coating. In an automatic embodiment, this situation will be detected by a signal processing unit, and an automatic or manual change-over to a fresh flow cell takes place.

The drain pipe from one biosensor flow cell may be directly connected to the inlet of another, thus adding sensitivity to a different analyte, such as an explosive or a narcotic, or a multisensor system or parallel biosensors can be arranged by dividing the inlet into an array of flow cells.

The crystal in the flow cell may be operated in such a way, that a pump function of the solution will accrue, thus eliminating the need for a separate pump in the second enrichment stage.

The Signal Processing Electronics contain electronics for operating the crystal, measurement of different parameters, control of the whole enrichment procedure and measurement of process and decision algorithms for the evaluation of the results. More precisely, it measures continuously the changes in the resonance frequency of the crystal(-s) in the biosensor(-s) and makes the necessary calculations to evaluate if the analyte, e.g. TNT, vapor is present in the tested air sample, and presents the result to the operator or operative system. To measure the small frequency changes in the biosensor, a high short to medium time precision time/frequency reference, in form of an OCXO (Oven Controlled Crystal Oscillator) or better, must be used. (Standard precision lab instrument was used in prototype).

The Central Processing Unit in the signal processing electronics will also supervise the power supply, the function of the biosensor, make automatic tests and calibrations, at start-up and at biosensor shifts, and evaluate and signal when the useful life of a biosensors is consumed.

The signal processing electronics will include a serial communication link, for communication with an external computer in a multi-sensor system, for detection and localization of analyte, or for testing, control and service.

The Man Machine Interface (MMI) is the operator's normal way of communication with the signal processing electronics when the biosensor system is used as a stand alone equipment, and no control commands are executed through the serial communication link. Presentation of equipment status and the results of the analysis (one type of sensors in use) are presented by 3 signal lamps or LED:s of different color and an acoustic warning signal from a beeper or through an earphone. A red lamp may be used to indicate detection of the analyte vapor and a green for a clear, i.e. that nothing is detected by the biosensor. In between there may also be a yellow lamp indicating an indifferent status, e.g. that more information/sampling is necessary for a reliable indication either way. Acoustic alarm shall accompany a rise in the risk—color shift from green to yellow (red) or yellow to red.

The operator's settings on the MMI are on-off, continuous—intermittent measurement and a measurement-0-test trigger.

In the prototype a PC (personal computer) was used for signal processing and the MMI simulated on its screen.

The support systems are the mechanical and the electrical structure of the unit and the power supply with batteries and voltage converters/regulators.

The mechanical structure may be a light, two-part design for one man, a backpack and a hand-held sniffer part. The backpack, with batteries and most of the electronics of the system, is connected via a cable to the sniffer part, which is hand-held but with a supporting body harness. Thus, the complete unit is a small light-weight unit that can be worn during a whole working day with low stress from the wearing.

The power pack can take batteries of different style, both primary and rechargeable. Power can also be fed from an outside (12 V DC) source. The recommended power source for field use, as a stand alone equipment, is primary cells of the "D"-size.

The support system for the demonstrator is standard laboratory and PC equipment.

The above disclosed biosensor system is designed to be the main sensor(-s) in single- or multisensor systems for the detection of an analyte in an air sample collected at a suspected location. The biosensor system is highly sensitive and selective and can be designed to detect vapor from a single analyte when antibodies directed to said analyte are used in the coating of the biosensor cell. The biosensor system may also contain several biosensors for detection of different analytes.

The disclosed biosensor system is designed to be as sensitive as a dog for the smell from the analyte but with higher reliability and availability at a reasonable cost.

DESCRIPTION OF THE DRAWINGS

FIG. 1 shows a cross-section of an air sampling system for collecting an air sample. A mouthpiece (10) is held at the suspected location, e.g. just above the ground, and the air is transported through an adsorption filter (11) of a first enrichment stage with the aid of an air pump, which is connected (13) to the backside of the filter, thus being less sensitive to contamination. After each sampling, the filter is moved to its next position (desorption) by a revolver (12);

FIG. 2a. shows a cross-section of a first enrichment stage comprising a adsorption-desorption filter. The filter comprises a winding (21) of a resistance wire, such as a metal wire, coated with an active (insulating) material having affinity for the tested analyte (e.g. a hydrophobic material) encased in a plastic housing (20) and with two circular connector bands (22) soldered to the ends of the wire, FIG. 2b. shows a perspective view of the first enrichment stage, where the solder joint can be seen;

FIGS. 4a and 4b show a schematic presentation of the function of a filter heater. To desorb the analyte (TNT) from the filter, the temperature is increased from ambient temperature to the desorption temperature. The heating is effected in a very short time, and the temperature is then held constant until the desorption is finished. This can be done without the use of a separate temperature sensor (which might disturb the adsorption of the analyte, TNT) by using the resistance (e.g. copper) wire in the filter as a thermometer. For example, copper has a good and well known temperature constant, i.e. the resistance in the filter wire will increase with the temperature. If the filter is operated with a known constant current, it is possible to measure the voltage drop in the winding and get a voltage potential to the temperature.

In FIG. 4a., the following functions are shown,
(1) the copper in the filter wire is heated to the desorption temperature,
(2) a constant current is generated,
(3) measurement of raw signal,
(4) the measurement of the raw signal is converted to a voltage which is proportional to the temperature in the filter, and it is adapted to control of the pulse wide modulator (PWM),
(5) a trigger signal indicates to the signal processing when the filter temperature shall be measured (heating current off),
(6) PWM signal for high power control (with the switch in off position only when the constant measurement current goes through the wire), and
(7) main heating current to filter wire.

FIG. 4b., shows schematically each of the signals (1)–(7).

EXPERIMENTS

A prototype of the above disclosed automated sampling system was use for the detection of TNT as the analyte.

EXAMPLE 1

A test amount of TNT was placed in a plastic bag which was fastened with tape on the inside wall of a suitcase.

A mouthpiece (10) was stuck into the suitcase, and air was sucked from the suitcase and passed through the first enrichment stage, i.e. an adsorption/desorption filter (20).

Adsorption

Suction Time: 10 sec.

Flow rate: 45 L/min.

Source: Suitcase, 50 L, with 10 g of TNT in a plastic bag

Filter: Copper wire with a plasma etched Teflon® coating.

Thermal desorption, i.e. electric current through the wire of the filter, liberates the TNT adsorbed on the surface of the wire coating, and during the desorption nitrogen gas is passed through the filter and carries the TNT vapors to the second enrichment stage, i.e. a cold trap, where TNT is condensed on the walls of the capillary (32).

Desorption

Desorption temperature: 200° C.

Desorption flow ($N_2$): 20 ml/min

Temperature in the cold trap: 25° C.

Material in the cold trap: quartz

The cold trap was emptied with the aid of a buffer solution which was introduced by injection with a syringe. The buffer solution dissolves the TNT. Then the solution was sucked from the cold trap with an injection syringe.

Buffer solution: 0.01 m Na-phosphate buffer, 0.1 NaCl, pH=7.4

Buffer volume: 10 $\mu$l

Time for emptying: 1 minute

Analysis of TNT Content by Gas Chromatography

Analysis of the TNT content in the cold trap was performed with a gas chromatograph having electron capture detection (GC-ECD).

The solution from the cold trap was placed on a wad of quartz wool in an air sampling tube. Before the injection started, the solvent was evaporated from the tube. Injection of samples were made by thermal desorption of the air sampling tube, simultaneously trapping the desorbed material in a cold trap, which subsequently was flashed heated (thermal desorption cold trap injector, TCT).

Instrument Parameters

Instrument: Chrompack CP-9001 GC integrated with CP 4001 TCT/PTI

GC column: 10 m×0.32 mm CP-Sil 5 CB (1.2 $\mu$m)

Carrier gas: Helium, 45 kPa

TCT conditions:
  Cold trap: −70° C.
  Desorption temp.: 250° C.
  Desorption time: 15 min
  Desorption flow: 35 ml/min
  Injection temp.: 200° C.
  Injection time: 1 min GC conditions:
  1 min at 150° C., followed by 150° C.→250° C., 10° C./min Detector: Electron capture detector (ECD)

Results: the yield of TNT was approximately 200 pg (relative standard deviation 30%).

EXAMPLE 2

The Example 1 was repeated but the analysis of the TNT content in the cold trap was performed with a biosensor system as described in the general part of this description.

A piezoelectric biosensor having a coating on the crystal comprising antibodies binding specifically to TNT was used for the detection of TNT in the solution from the cold trap.

Results: TNT could still be detected at the low level of 10 picograms.

EXAMPLE 3

The sampling system described in Example 1 was used for determination of the influence of the desorption time on the total efficacy. The test parameters were as follows Adsorption
Suction time: 30 sec.
Flow rate: approx. 1 L/sec.
Source: Wooden box with 10 g of TNT
Filter: Copper wire with a plasma etched Teflon® coating.
Desorption
Desorption temperature: 200° C.
Desorption flow ($N_2$): 20 ml/min
Heating time: 3 sec.
Deasorption time: 3, 18 or 120 sec.
Emptying of the Cold Trap
Solvent: Acetone
Volume added: 3 µl
Volume extracted: approx. 1.5 µl (the rest had evaporated)
Analysis
Analysis on GC-ECD (cf. Example 1) (Split injection)
Results
The results are summarized in Table 1.

TABLE 1

Analyzed contents of TNT at different desorption times

| Desorption time | TNT content (ng) |
|---|---|
| 3 | 0.45 |
| 3 | 0.61 |
| 18 | 0.87 |
| 18 | 1.04 |
| 120 | 0.82 |
| 120 | 0.99 |

The results in Table 1 indicate that a desorption time of 18 sec. is sufficient for obtaining the same yield as at longer desorption times. Already at 3 sec. 60% of the yield is obtained. An optimization of the parameters should result in a reduction of the desorption time to at most 18 sec. with retained efficacy.

EXAMPLE 4

This experiment was conducted for the purpose of finding out if the air above real mines buried in the ground detecting contains detectable amounts of TNT.

The samples were collected in South Africa in the vicinity of an anti-tank mine (AT mine) with the aid of an absorption/desorption filter according to the invention inserted into an air sampling equipment of Mechem.

Samples were taken at a position just above the mine, walking past the mine and along a section of road which had been classified as mine free. (The AT mine was also placed on a section of the road). The absorption/desorption filters were sent to use in Sweden for analysis. The sampling was made in a blind way, i.e. without giving the knowledge to use before analysis.

Adsorption
Suction time: 1, 2 or 4 min.
Flow rate: approx. 1 L/sec.
Source: see above
Filter: Copper wire with a plasma etched Teflon® coating
Desorption
Desorption temperature: 200° C.
Desorption flow ($N_2$): 20 ml/min
Deasorption time: 60 sec.
Emptying of the cold trap
Solvent: Acetone
Volume added: 3 µl
Volume extracted: approx. 1.5 µl (the rest had evaporated)
Analysis
Analysis from acetone on GC-ECD (cf. Example 1) (Split Injection)
Results
The results are summarized in Table 2.

TABLE 2

Summary of the results from the tests in South Africa

| Sample | TNT content (pg) | Collected volume of air (liter) | TNT content per collected volume of air (pg/L) |
|---|---|---|---|
| AT mine, just above | 150 | 60 | 2.5 |
| AT mine, walking by | 330 | 120 | 2.7 |
| Mine free road | 30 | 240 | 0.1 |

The reason for the low content of TNT on the mine free section of road is not known, but may be due to contamination during transport of the filters to Sweden.

These initial results from real mine testing show that it is possible to decide which section of a road is mine free with the detection system using air sampling and an adsorption/desorption filter of the invention.

What is claimed is:

1. Apparatus for the detection of an analyte in air comprising an air sampling system for collecting an air sample comprising a funnel or nozzle and a fan, means for transport of the air through a first enrichment stage for enrichment of the analyte comprising a thermally regulated adsorption/-desorption filter creating a non-laminar gas flow for adsorption of the analyte on the filter surfaces, encased in a housing having a gas inlet and a gas outlet connected to a revolver, and a heat source for heating the filter to a temperature high enough to evaporate the analyte but low enough to avoid decomposition of the analyte, means for transport of the desorbed analyte from the filter to a second enrichment stage for the further enrichment of the gaseous analyte comprising a cold trap for condensing the analyte, means for extraction of the condensed material with a solvent, and means for collecting the resulting solution of condensed material and solvent enriched in analyte from the cold trap, and means for transport of the collected liquid sample to an analytical detection system for the detection of the analyte.

2. Apparatus for the detection of an analyte in air according to claim 1, wherein the first enrichment stage is reconditioned by cooling gas, and the second enrichment stage is connected to a second revolver and reconditioned by washing the cold trap with a solvent.

3. System for the detection of an analyte in air comprising an air sampling system comprising a funnel or nozzle and a fan, a first enrichment stage for enrichment of the analyte comprising a thermally regulated adsorption/desorption filter creating a non-laminar gas flow comprising a housing having a gas inlet and a gas outlet connected to a revolver, and a heat source for heating the adsorption/desorption filter to a temperature high enough to evaporate the analyte but low enough to avoid decomposition of the analyte, a second enrichment stage for additional enrichment of the analyte comprising a cold trap for condensing the analyte, extraction of the condensed material with a solvent, and collecting the resulting solution of condensed material and solvent enriched in analyte from the cold trap, and an analytical detection system for the detection of the analyte from a liquid sample.

4. System for the detection of an analyte in air according to claim 3, wherein the first enrichment stage is reconditioned by cooling gas, and the second enrichment stage is connected to a second revolver and reconditioned by washing the cold trap with a solvent.

5. Method of detecting an analyte in air comprising sampling of air with an air sampling system comprising funnel or nozzle and a fan, passing the air to a first enrichment stage where the analyte is adsorbed on the surfaces of a thermally regulated adsorption/desorption filter creating a non-laminar gas flow, heating the filter surfaces to a temperature high enough to evaporate the analyte but low enough to avoid decomposition of the analyte, flushing the filter with a small amount of an inert gas, passing the vapor from the first enrichment stage to a second enrichment stage for the further enrichment of the analyte by condensation in a cold trap, flushing the cold trap with a small amount of solvent to dissolve the condensed material, collecting the resulting small amount of solution of solvent and condensed material containing the analyte in an container, and analyzing the presence of analyte in the container with the aid of an analytical detection system for the detection of the analyte in liquid sample.

6. Method of detecting an analyte in air according to claim 5, wherein the analyte is a gaseous component of explosives or mines.

* * * * *